(12) United States Patent
Skarda

(10) Patent No.: US 7,156,843 B2
(45) Date of Patent: Jan. 2, 2007

(54) IRRIGATED FOCAL ABLATION TIP

(75) Inventor: James R. Skarda, Lake Elmo, MN (US)

(73) Assignee: Medtronic, Inc., Minneapolis, MN (US)

(*) Notice: Subject to any disclaimer, the term of this patent is extended or adjusted under 35 U.S.C. 154(b) by 314 days.

(21) Appl. No.: 10/657,377

(22) Filed: Sep. 8, 2003

(65) Prior Publication Data

US 2005/0055020 A1 Mar. 10, 2005

(51) Int. Cl.
*A61B 18/18* (2006.01)

(52) U.S. Cl. .......................... 606/41; 607/105

(58) Field of Classification Search .............. 607/99, 607/101–102, 113, 104–106; 606/27, 33, 606/41, 44, 42, 45–50; 604/114, 117, 118, 604/20–22
See application file for complete search history.

(56) References Cited

U.S. PATENT DOCUMENTS

| | | | | |
|---|---|---|---|---|
| 5,334,193 A | 8/1994 | Nardella | ...................... | 606/41 |
| 5,348,554 A | 9/1994 | Imran et al. | .................. | 606/41 |
| 5,423,811 A | 6/1995 | Imran et al. | .................. | 606/41 |
| 5,462,521 A | 10/1995 | Brucker et al. | ................ | 604/20 |
| 5,545,161 A | 8/1996 | Imran | .......................... | 606/41 |
| 5,643,197 A | 7/1997 | Brucker et al. | ................ | 604/20 |
| 5,676,662 A * | 10/1997 | Fleischhacker et al. | ....... | 606/41 |
| 5,913,854 A | 6/1999 | Maguire et al. | ............... | 606/41 |
| 6,016,809 A | 1/2000 | Mulier et al. | ............... | 128/898 |
| 6,280,441 B1 | 8/2001 | Ryan | ........................... | 606/45 |
| 6,332,881 B1 | 12/2001 | Carner et al. | .................. | 606/41 |
| 6,358,247 B1 * | 3/2002 | Altman et al. | ................ | 606/41 |
| 6,488,680 B1 | 12/2002 | Francischelli et al. | ........ | 606/41 |
| 6,497,704 B1 * | 12/2002 | Ein-Gal | ........................ | 606/41 |
| 6,537,248 B1 * | 3/2003 | Mulier et al. | ............... | 604/114 |

FOREIGN PATENT DOCUMENTS

WO  WO 96/39966  12/1996

* cited by examiner

*Primary Examiner*—Roy D. Gibson
(74) *Attorney, Agent, or Firm*—Michael C. Soldner; Carol F. Barry; Girma Wolde-Michael

(57) ABSTRACT

A helical ablation electrode extends from a distal end of the shaft and includes a first portion extending from a first end winding about a first diameter, a second portion extending from the first portion and winding about a second diameter smaller than the first diameter, and a second end terminating the second portion. The electrode further includes a fluid lumen extending from a location in proximity to the first end of the electrode to a location in proximity to the second end of the electrode and in fluid communication with a fluid delivery lumen of the catheter shaft. An irrigation fluid delivered through the fluid delivery lumen of the catheter shaft, from a fluid port, passes through the fluid lumen of the ablation electrode to cool the electrode.

39 Claims, 12 Drawing Sheets

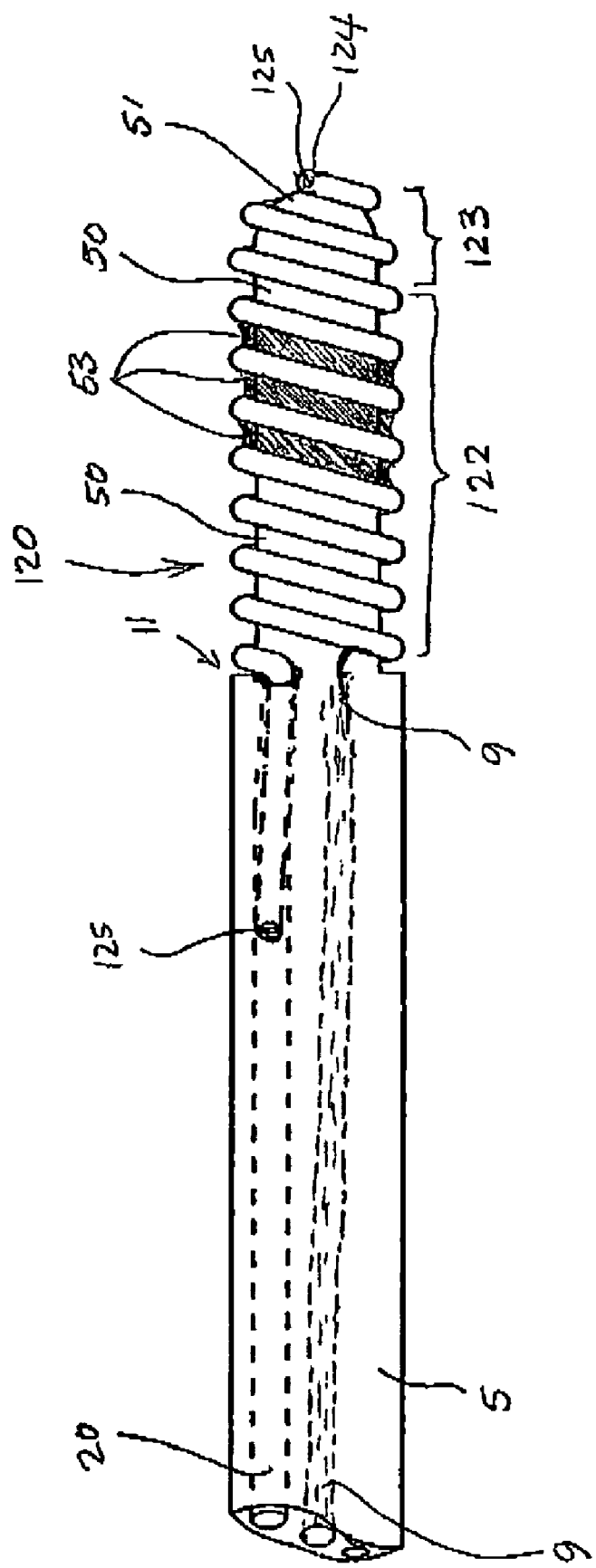

IRRIGATED FOCAL ABLATION TIP

TECHNICAL FIELD

The present invention relates to catheters for delivery of ablative energy and more particularly to irrigated focal ablation tips for such catheters.

BACKGROUND

Therapies have been developed for treating atrial and ventricular tachycardias by destroying cardiac tissue containing an identified ectopic foci or an aberrant conduction pathway; one of these therapies includes the application of ablative RF energy delivered through a catheter, which may be introduced transvenously into the heart, via a catheter electrode in direct contact with the arrhythmogenic site of the cardiac tissue. Because of the nature of RF energy, both the electrode contacting the tissue and the tissue are heated simultaneously; the amount of tissue heating that occurs is dependent upon the area of contact between the electrode and the tissue and the impedance between the electrode and the tissue, the lower the impedance the greater the tissue heating. An electrode that is actively cooled by an irrigating fluid is more efficient in the transmission of ablative energy into the tissue and reduces the potential for complications arising from an excessive electrode temperature (approximately greater than 100 degrees Celsius) that may cause formation of blood coagulum and sub-surface explosions or pops within the tissue.

Physicians have long used the technique of pressing against the endocardium an ablation element mounted on a distal end of a catheter, applying ablation energy, and dragging the electrode along the endocardium to create an elongated lesion. Consequently, there remains a need for an improved ablation catheter including an irrigated tip electrode that is simple to fabricate and to use efficaciously in this manner.

BRIEF DESCRIPTION OF THE DRAWINGS

The following drawings are illustrative of particular embodiments of the invention and therefore do not limit its scope, but are presented to assist in providing a proper understanding of the invention. The drawings are not to scale (unless so stated) and are intended for use in conjunction with the explanations in the following detailed description. The present invention will hereinafter be described in conjunction with the appended drawings, wherein like numerals denote like elements, and:

FIGS. 3A–B are plan views of distal portions of ablation catheters according to alternate embodiments of the present invention;

DETAILED DESCRIPTION

The following detailed description is exemplary in nature and is not intended to limit the scope, applicability, or configuration of the invention in any way. Rather, the following description provides a practical illustration for implementing exemplary embodiments of the invention. Although embodiments of the present invention are presented in the context of RF ablation, it should be noted that other ablative therapies, for example microwave ablation and cryo-ablation, may be delivered in conjunction with fluid flow through electrodes conforming to embodiments of the present invention.

Figure 1:
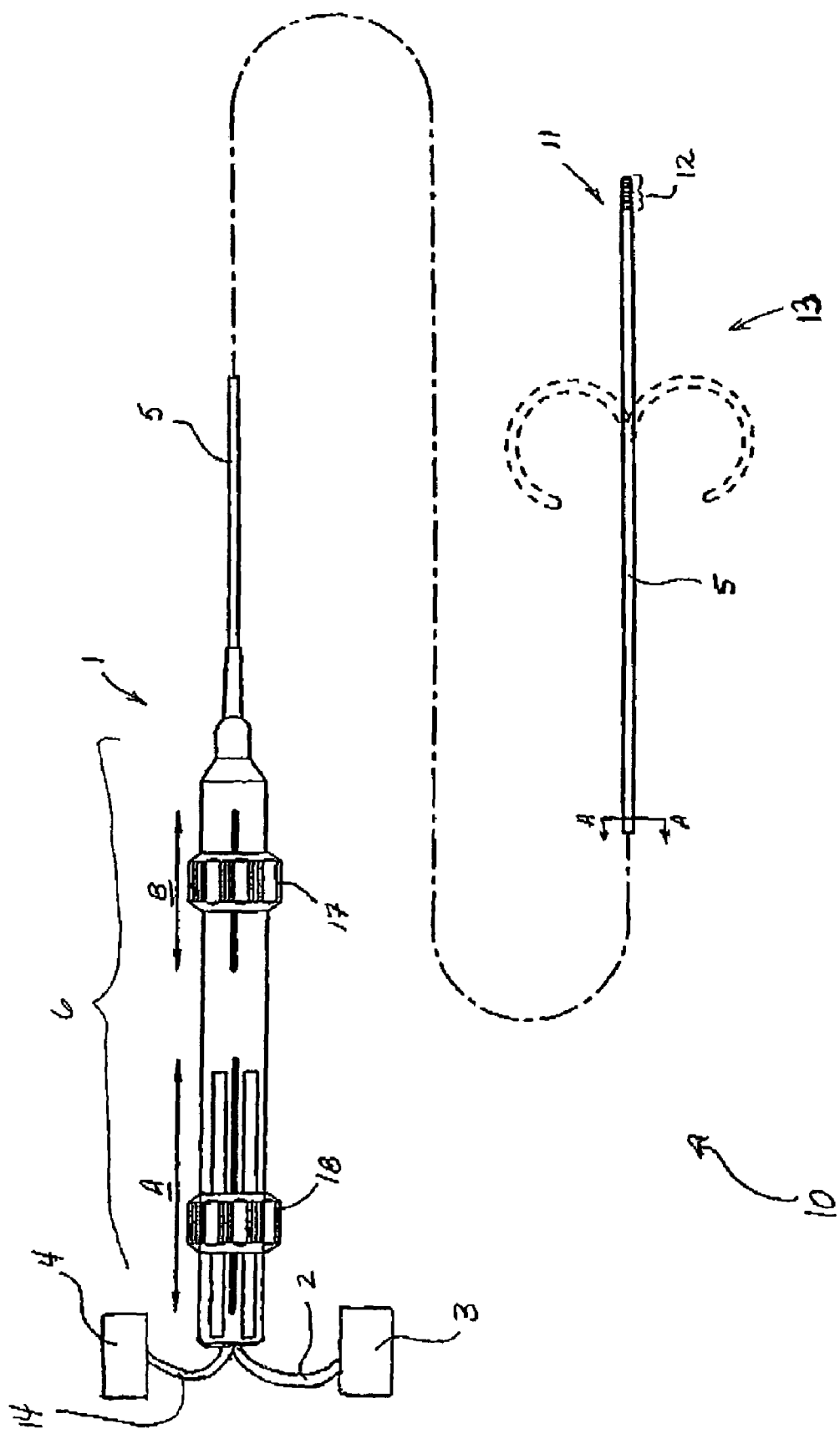
FIG. 1 is a schematic over-view of an ablation system according to one embodiment of the present invention.

FIG. 1 is a schematic over-view of an ablation system according to one embodiment of the present invention. FIG. 1 illustrates the ablation system including a catheter 10 coupled to an electro-surgical unit 4, via electrical terminals 14 of a catheter handle 6, and to a fluid source 3 via a port 2 extending from handle 6; handle 6 terminates a proximal end 1 of a catheter shaft 5 and further includes controls 17 and 18 adapted to create a curve (indicated in two directions by dashed lines) in a distal portion 13 of catheter 10—control 17 sliding per arrow A to control a radius of the curve (via radius wire 8 illustrated in FIGS. 2A–B) and control 18 sliding per arrow B to actuate the curve in either direction (via pull wire 7 also illustrated in FIGS. 2A–B). Such means for deflecting distal portions of catheter shafts are well known to those skilled in the art and are not necessary elements of embodiments according to the present invention. FIG. 1 further illustrates distal portion 13 of shaft 5 including a distal end 11 and a helical ablation electrode 12 extending distally from distal end 11. According to embodiments of the present invention, helical ablation electrode 12, coupled to distal end 11 of shaft 5, includes a fluid lumen in communication with one or more fluid delivery lumens of shaft 5, as will be further described below. Shaft 5 may be formed from a biocompatible polymer, including, for example a polyethylene or a polyimide, and may be between approximately 5 Fr (1.6 mm) and approximately 10 Fr (3.3 mm) in diameter, having a length between approximately 60 cm and approximately 70 cm. Electrode 12 may be formed of any conductive tubing, examples of which include but are not limited to stainless steel and platinum-iridium, a radial cross-section of which may take on any shape, examples of which include circular, oval, and rectangular. Additional appropriate materials and methods used in the construction of ablation catheters are well known to those skilled in the art.

Figure 2B:
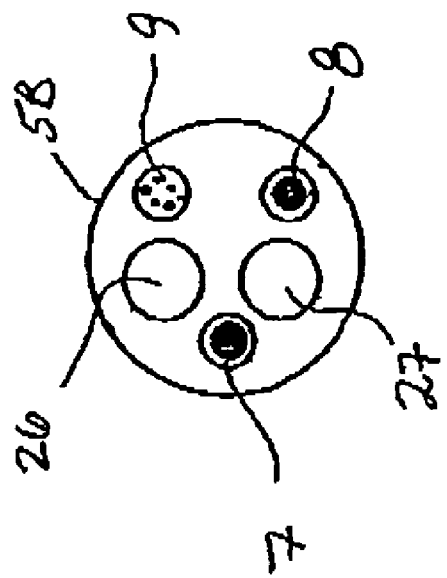
FIGS. 2A–B are section views, taken through section line A—A of FIG. 1, according to alternate embodiments of the present invention.
Figure 2A:
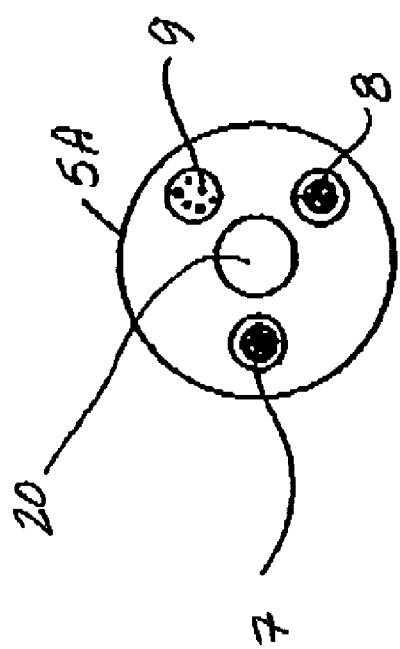

FIGS. 2A–B illustrate alternative catheter shafts 5A and 5B, according to alternate embodiments of the present invention, and are section views taken through section line A—A of FIG. 1. FIGS. 2A–B illustrate both shaft 5A and shaft 5B including insulated electrical wires 9, a radius wire 8 and a push-pull wire 7; however, shaft 5A includes a single fluid delivery lumen 20 while shaft 5B includes two fluid delivery lumens 26 and 27. Insulated electrical wires 9 couple electro-surgical unit 4 to helical ablation electrode 12 to deliver ablative energy, and to thermocouples and/or thermistors (not shown), mounted in proximity to electrode 12, to monitor temperatures. Fluid lumen 20 or, alternately, lumens 26 and 27 couple fluid source 3 to helical ablation electrode 12 to deliver a cooling irrigation fluid through electrode 12. One embodiment of fluid source 3 includes a standard issue hospital grade pump, which delivers fluid at a rate between approximately 100 ml/hr and approximately 1000 ml/hr to cool electrode 12 as ablative energy is delivered to electrode 12. Catheter assemblies including a single fluid delivery lumen, e.g. lumen 20, are described herein in conjunction with FIGS. 3A–B, 5A–B and 6A, while catheter assemblies including two fluid delivery lumens, e.g. lumens 26, 27, are described in conjunction with FIG. 6C. Although port 2, joining fluid lumen 20 or, alternately, lumens 26 and 27 to fluid source is illustrated in FIG. 1 as extending from a proximal end of handle 6, according to alternate embodiments, a fluid port may extend from another portion of handle 6 or may extend from shaft 5 at a location distal to handle 6. According to yet another embodiment, another fluid port coupled to fluid delivery lumen 20, 26, or 27 is incorporated for secondary delivery of alternate fluids through electrode 12, for example therapeutic agents and contrast media for X-ray visualization.

Figure 3A:
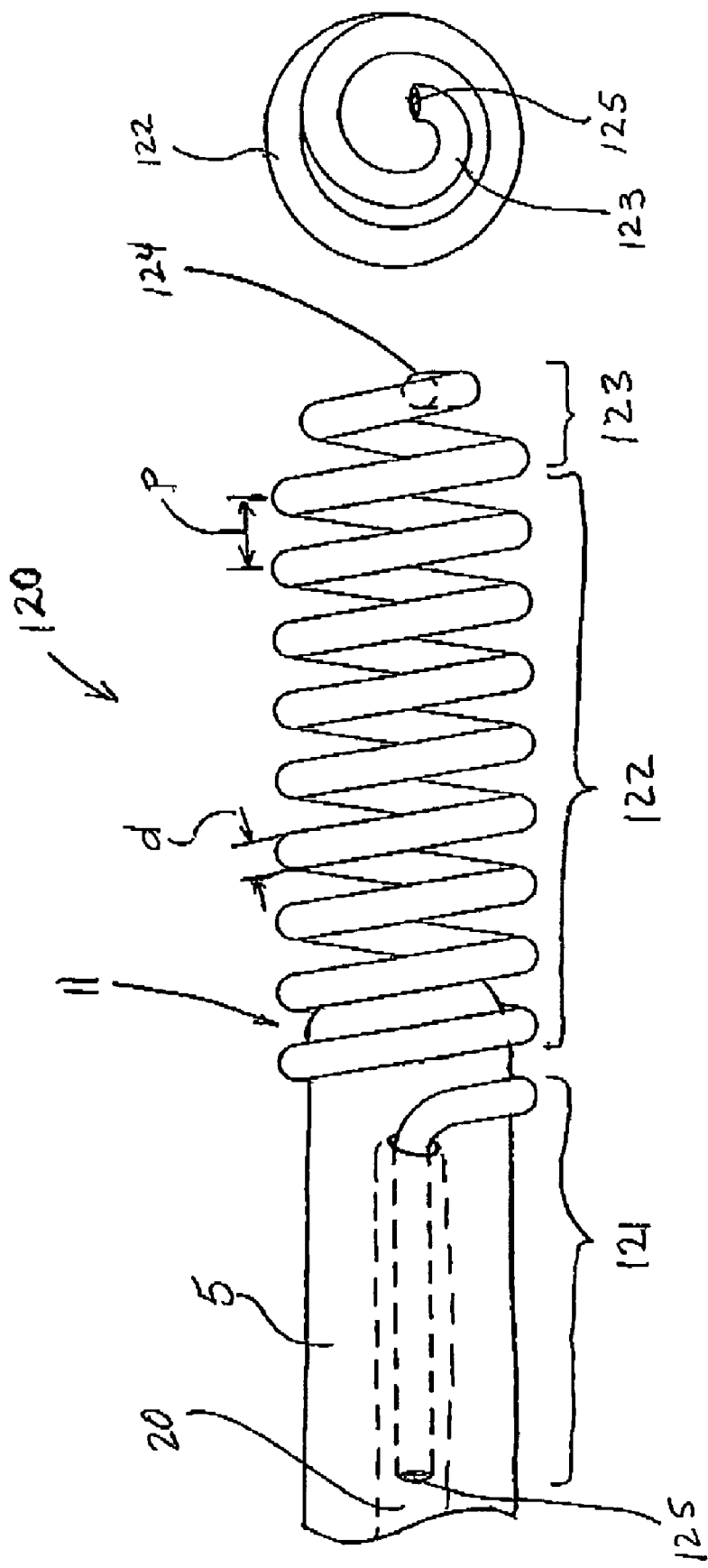

FIGS. 3A–B are plan views of distal portions of ablation catheters according to alternate embodiments of the present invention. FIG. 3A further includes an end view and illustrates a helical ablation electrode 120 extending distally from distal end 11 of catheter shaft 5; electrode 120 includes a first end 121, a first portion 122 extending from first end 121 and winding around a first diameter, a second portion 123 extending from first portion 122 and winding around a second diameter smaller than the first diameter, a second end 124 terminating second portion 123, and a fluid lumen 125 extending through electrode 120 making it a generally tubular structure having an inner diameter of approximately 0.01 inch according to one embodiment and up to approximately 0.05 inch according to alternate embodiments. According to one embodiment of the present invention, as illustrated in FIG. 3A, a portion of first end 121 of electrode 120 is contained within fluid delivery lumen 20 and provides fluid communication between delivery lumen 20 and fluid lumen 125, which extends through first end 121, first portion 122, second portion 123 and second end 124. The fluid may be delivered from fluid source 3 through port 2 (FIG. 1) and into delivery lumen 20 of catheter shaft 5 to cool electrode 120 by passing through fluid lumen 125, entering in proximity to first end 121 and exiting lumen 125, exterior to shaft 5, in proximity to second end 124. Fluid orifices of electrode 120 and other electrode embodiments described herein are sized in order to facilitate fluid flow for either even or gradient cooling along a length of the electrode. Furthermore, a pair of wires from insulated electrical wires 9 (FIGS. 2A and 3B) are coupled to ablation electrode 120, via mechanical crimping or staking or welding or any other means known to those skilled in the art, either passing from their respective lumen into lumen 20 or passing outside shaft 5 from their respective lumen, in order to power ablation electrode 120.

FIG. 3B illustrates an alternate embodiment wherein catheter shaft 5 includes a tip 50, extending from distal end 11, around which first and second portions 122, 123 of ablation electrode 120 wind. FIG. 3B further illustrates a dome shaped end 51, which tapers in alternate forms according to alternate embodiments, terminating tip 50 over which second portion 123 of electrode 120 winds in a decreasing diameter such that second end 124 is positioned in proximity to a centerline of tip 50, not necessarily aligned with the centerline. According to some embodiments, second end 124 is recessed into tip 50 creating a generally smooth surface terminating tip 50. FIG. 3B further illustrates insulated electrical wires 9 extending within another lumen of shaft 5 and coupled to electrode 120 as previously described.

FIG. 3A further illustrates a diameter d of tube forming electrode 120 and a pitch p defining a gap between winds or turns of electrode 120. According to one embodiment of the present invention, diameter d is approximately equal to 0.014 inch (approximately 0.36 millimeters) and pitch p is approximately equal to 0.028 inch (approximately 0.72 millimeters). According to an alternate embodiment, electrode 120 is close or tight wound such that pitch p is approximately equal to diameter d, leaving little or no gap between winds of electrode 120. A length of electrode, including first and second portions 122, 123 is approximately 8 millimeters (approximately 0.3 inch) according to one embodiment but may range between approximately 2 millimeters and 5 centimeters according to alternate embodiments. FIG. 3B further illustrates a filler material 53 filling gaps between windings of electrode 120; filler material 53 may serve a variety of purposes, examples of which include but are not limited to: securing electrode 120 to tip 50; creating a smoother surface between turns of electrode 120; increasing a surface area of electrode 120; modifying heat transfer characteristics of electrode 120; and securing thermocouples and/or thermistors (not shown) in proximity to portions of electrode 120. According to one embodiment filler material 53 comprises a polymer adhesive and according to another embodiment filler material 53 further comprises a conductive material in particulate form blended into the adhesive, while in yet another embodiment filler material 53 may be formed by a flux generated by, for instance welding turns of electrode 120 or of a flux material added to aid in welding turns of electrode 120. Although FIG. 3A illustrates filler material 53 filling three gaps between windings of electrode 120, embodiments of the present invention include filler material 53 between a single gap or a plurality of gaps fewer or greater than three. In yet another embodiment, as partially illustrated in FIG. 7, filler material 53 comprises ridges along the tip resulting from helical grooves formed in the tip to accommodate the helical ablation electrode.

Figure 4:
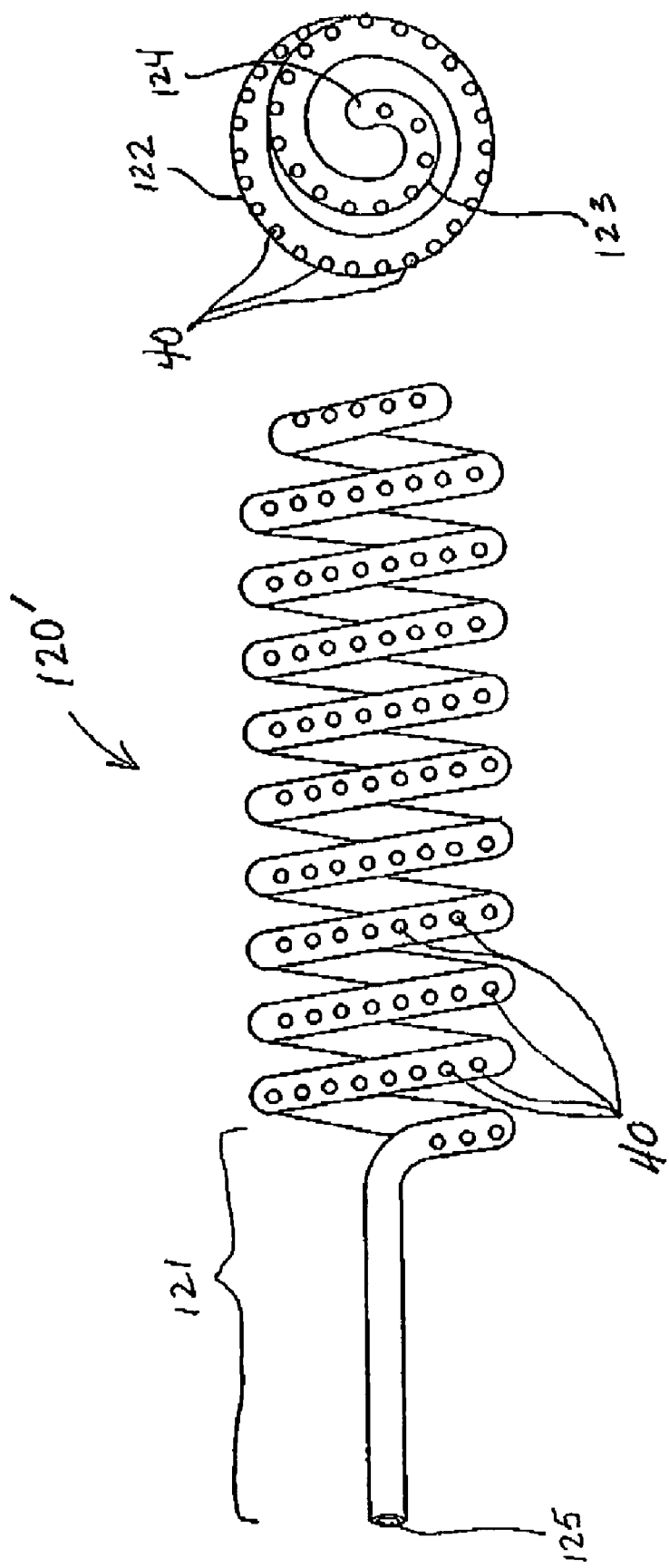
FIG. 4 is a plan and end view of an irrigated ablation electrode according to another embodiment.

FIG. 4 is a plan view of an irrigated ablation electrode according to another embodiment. FIG. 4 illustrates a helical ablation electrode 120' including a plurality of fluid exit ports 40 extending between lumen 125 and an exterior surface of electrode 120'. According to the embodiment illustrated in FIG. 4, a portion of first end 121 would be contained within a fluid delivery lumen of a catheter shaft, for example lumen 20 of shaft 5, to provide fluid communication between delivery lumen 20 and fluid lumen 125; lumen 125 at distal end 124 of electrode 120' is closed off so that cooling fluid would flow from the delivery lumen into fluid lumen 125 and out exit ports 40, which are sized in order to facilitate fluid flow for either even or gradient cooling along a length of the electrode.

Figure 5A:
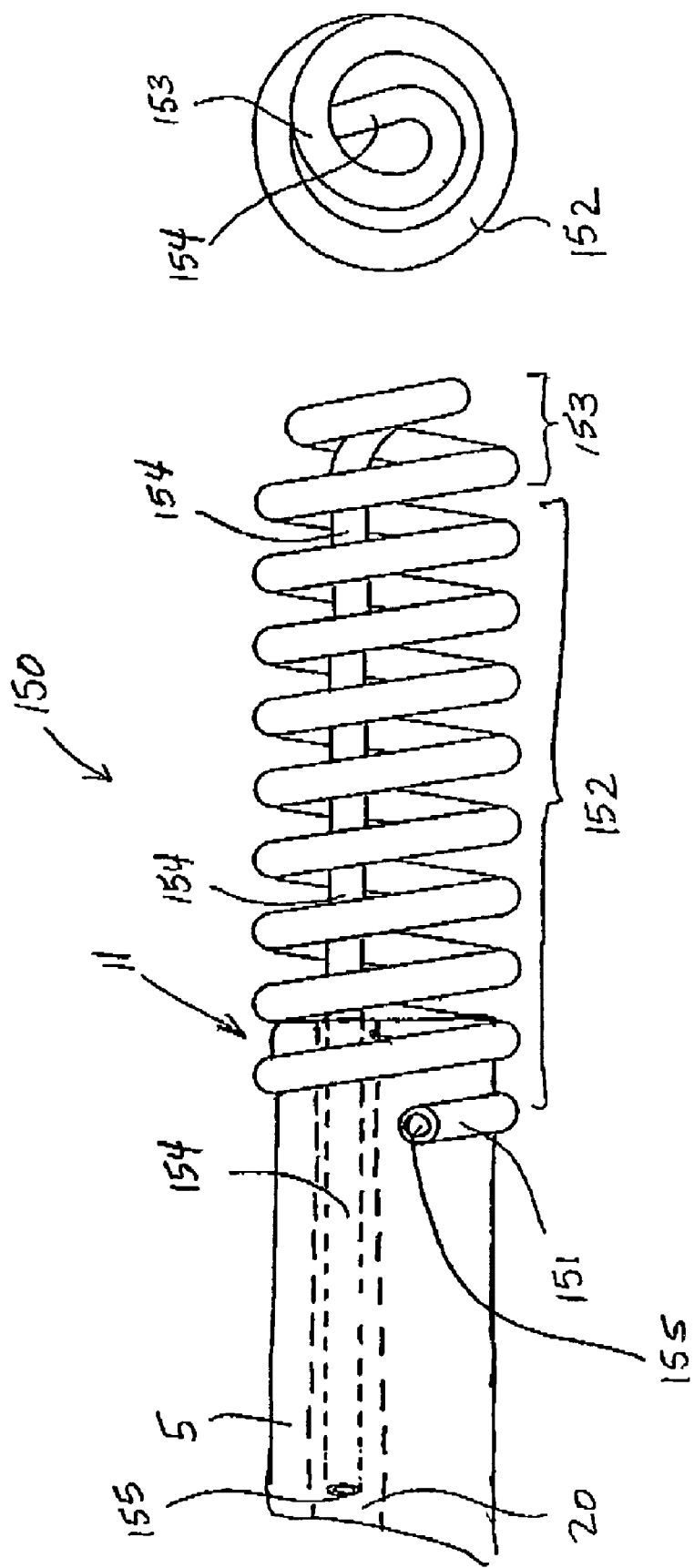
FIGS. 5A–B are plan views of distal portions of ablation catheters according to additional alternate embodiments of the present invention.
Figure 5B:
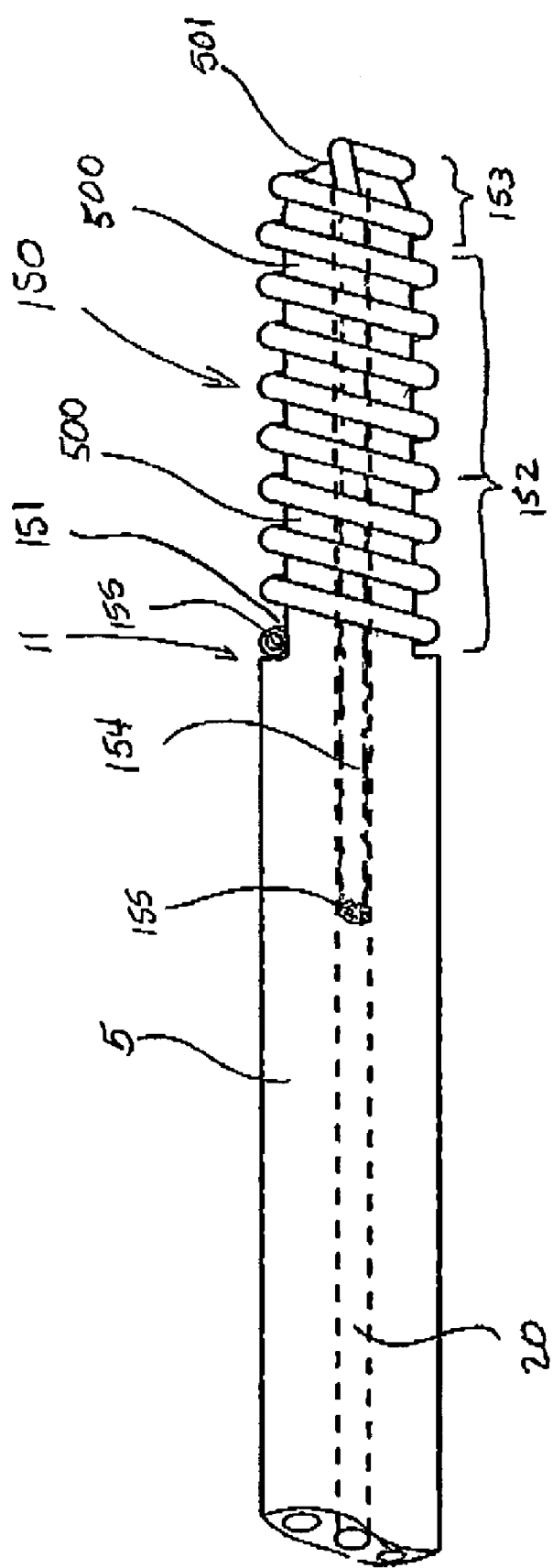

FIGS. 5A–B are plan views of distal portions of ablation catheters according to additional alternate embodiments of the present invention. FIG. 5A illustrates a helical ablation electrode 150 extending distally from distal end 11 of catheter shaft 5; electrode 150 includes a first end 151, a first portion 152 extending from first end 151 and winding around a first diameter, a second portion 153 extending from first portion 152 and winding around a second diameter smaller than the first diameter, a second end 154 terminating second portion 153, and a fluid lumen 155 extending through electrode 150 making it a generally tubular structure. According to one embodiment of the present invention, as illustrated in FIG. 5A, a portion of second end 154 of electrode 150 is contained within fluid delivery lumen 20 and provides fluid communication between delivery lumen 20 and fluid lumen 155, which extends through second end 154, second portion 153, first portion 152 and first end 151. Fluid may be delivered from fluid source 3 through port 2 (FIG. 1) and into delivery lumen 20 of catheter shaft 5 to cool electrode 150 by passing through fluid lumen 155, entering in proximity to second end 154 and exiting lumen 155, exterior to shaft 5, in proximity to first end 151. Furthermore, a wire from insulated electrical wires 9 (FIG. 2A) is coupled to ablation electrode 150, for example by laser welding or soldering, either passing from their respective lumen into lumen 20 or passing outside shaft 5 from their respective lumen, to power ablation electrode 150.

FIG. 5B illustrates an alternate embodiment wherein catheter shaft 5 includes a tip 500, extending from distal end 11, around which first and second portions 152, 153 of ablation electrode 150 wind. FIG. 5B further illustrates a dome shaped end 501, which tapers in an alternate forms according to alternate embodiments, terminating tip 500 over which second portion 153 of electrode 150 winds in a decreasing diameter such that second end 154 is positioned in proximity to a centerline of tip 500 and extends within lumen 20 which extends into tip 500. In an alternate embodiment, a filler material such as filler material 53 described in conjunction with FIG. 3B fills one or more gaps between windings of ablation electrode 150.

An alternate embodiment of electrode 150 depicted in FIG. 5A–B includes a plurality of fluid exit ports similar to those depicted in FIG. 4 wherein fluid lumen 155 is closed off at first end 151 so that cooling fluid would flow into lumen 155 in proximity to second end 154 and out from lumen 155 at the exit ports.

Figure 6A:
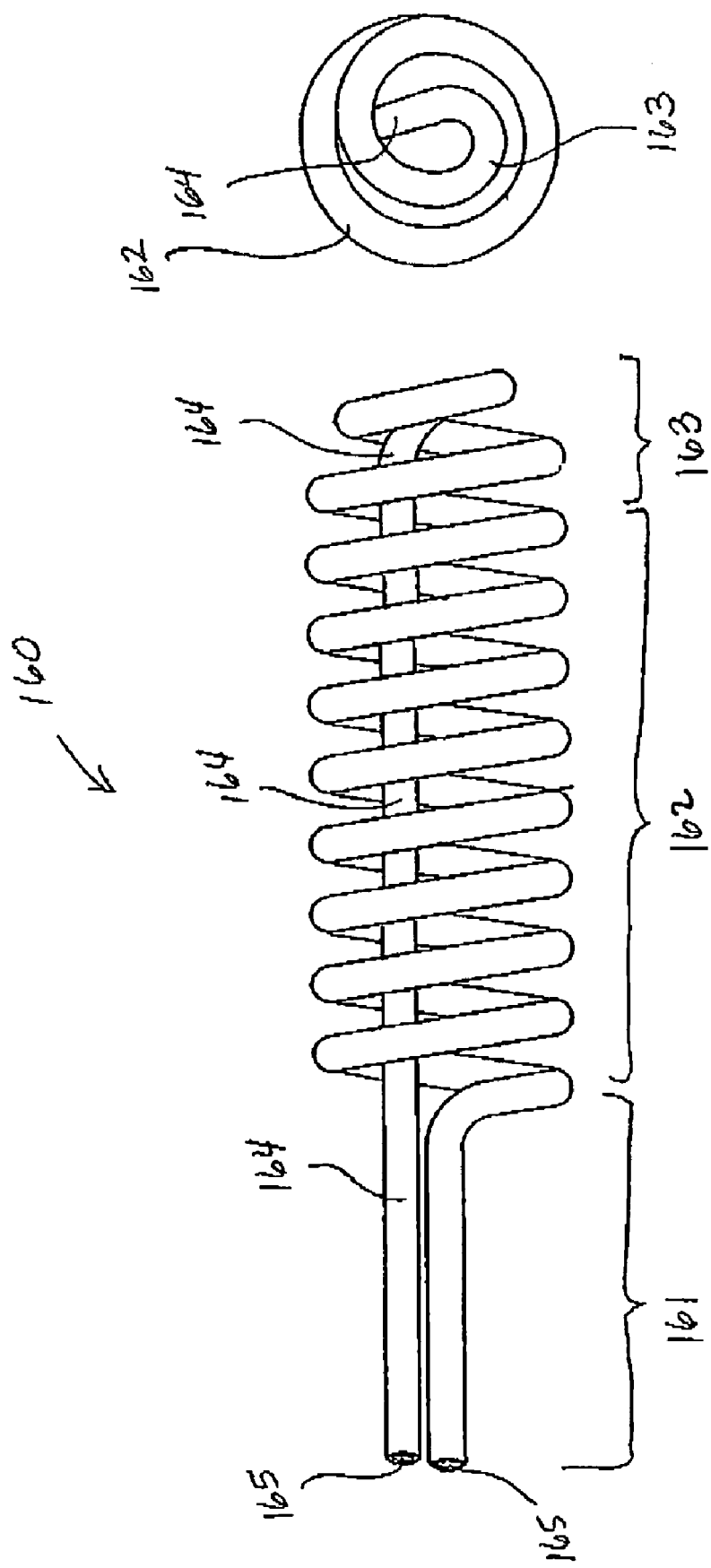
FIG. 6A is a plan and end view of an irrigated ablation electrode according to yet another embodiment of the present invention.
Figure 6B:
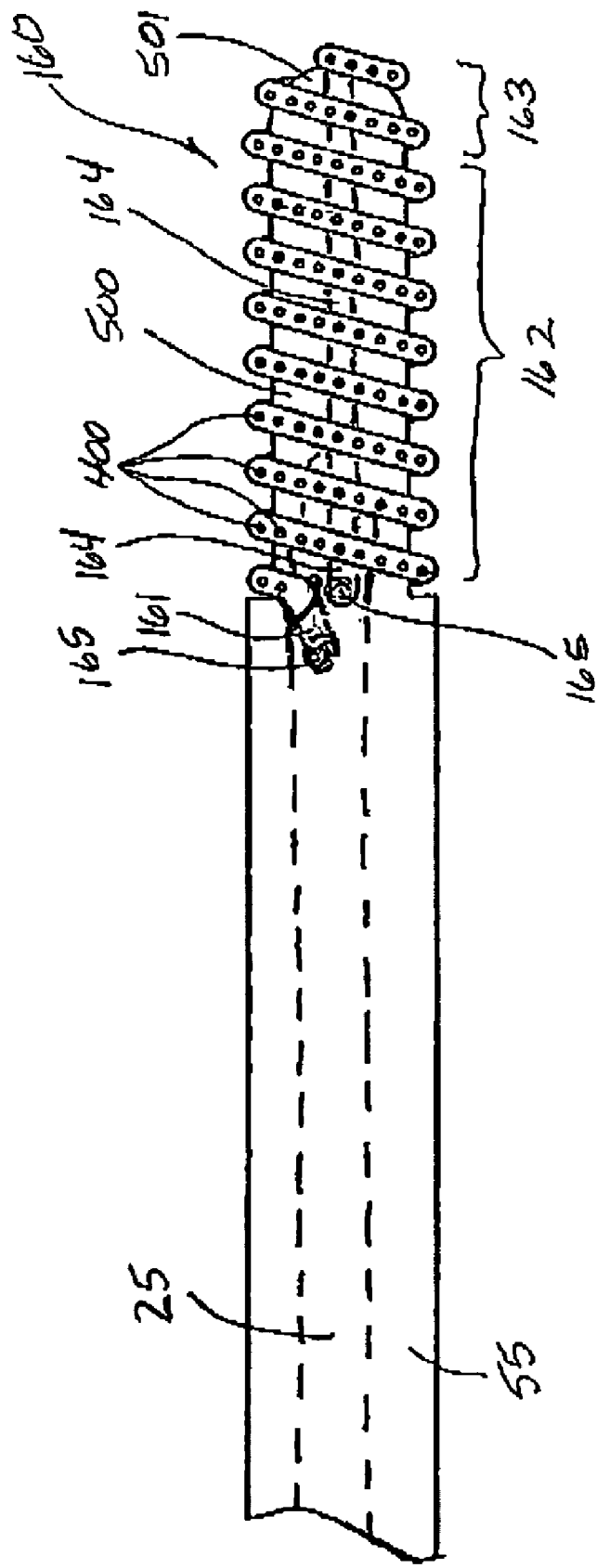
FIGS. 6B–C are plan views of alternate embodiments of distal portions of ablation catheters incorporating electrodes similar to that shown in FIG. 6A.
Figure 6C:
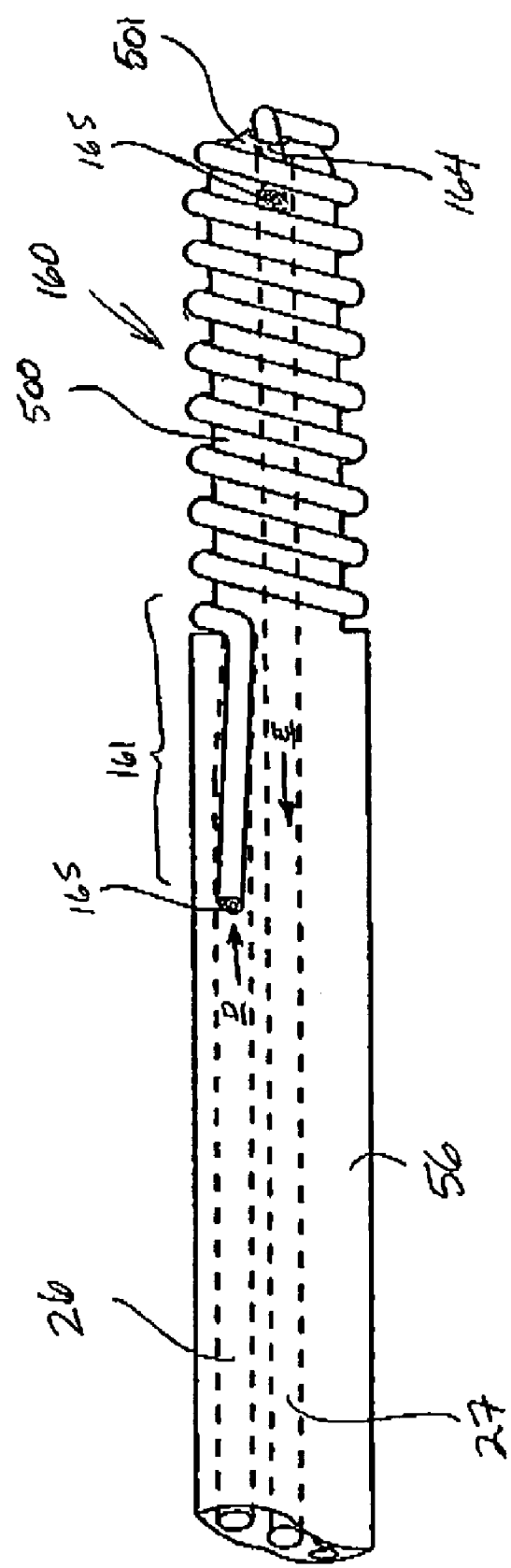

FIG. 6A is a plan view of an irrigated ablation electrode according to yet another embodiment of the present invention; and FIGS. 6B–C are plan views of alternate embodiments of distal portions of ablation catheters incorporating electrodes similar to that shown in FIG. 6A. FIG. 6A illustrates a helical ablation electrode 160 including a first end 161, a first portion 162 extending from first end 161 and winding around a first diameter, a second portion 163 extending from first portion 162 and winding around a second diameter smaller than the first diameter, a second end 164 terminating second portion 163, and a fluid lumen 165 extending through electrode 160 making it a generally tubular structure. FIG. 6B illustrates first and second ends 161, 164 of electrode 160 enclosed within a fluid delivery lumen 25 of a catheter shaft 55 to provide fluid communication between fluid lumen 165 and fluid delivery lumen 25, and electrode 160 further including a plurality of exit ports 400. According to embodiments of the present invention, fluid may be delivered from fluid source 3 through port 2 (FIG. 1) and into delivery lumen 25 of catheter shaft 55 to cool electrode 160 by passing through fluid lumen 165, entering at two points, in proximity to first end 161 and second end 164, and exiting lumen 155, exterior to shaft 5, at fluid exit ports 400. Although FIG. 6B illustrates catheter shaft 55 including a tip 500 around which first and second portions 162, 163 of electrode 160 wind, an alternate embodiment of the present invention does not include tip 500 (similar to that shown in FIG. 5A).

FIG. 6C illustrates an ablation catheter shaft 56 including a first fluid delivery lumen 26 enclosing a portion of first end 161 of electrode 160 and a second fluid delivery lumen 27 enclosing a portion of second end 164. According to embodiments of the present invention, port 2 (FIG. 1) includes a first port sending fluid from fluid source 3 into fluid lumen 165 of electrode 160 via first fluid delivery lumen 26 per arrow D and a second port receiving the fluid, which has passed through lumen 165, back into fluid source 3 via second fluid delivery lumen 27 per arrow E. According to an alternate embodiment, the direction of fluid flow is reversed, such that fluid enters fluid lumen 165 of electrode 160 in proximity to second end 164 and exits fluid lumen 165 in proximity to first end 161.

Figure 7:
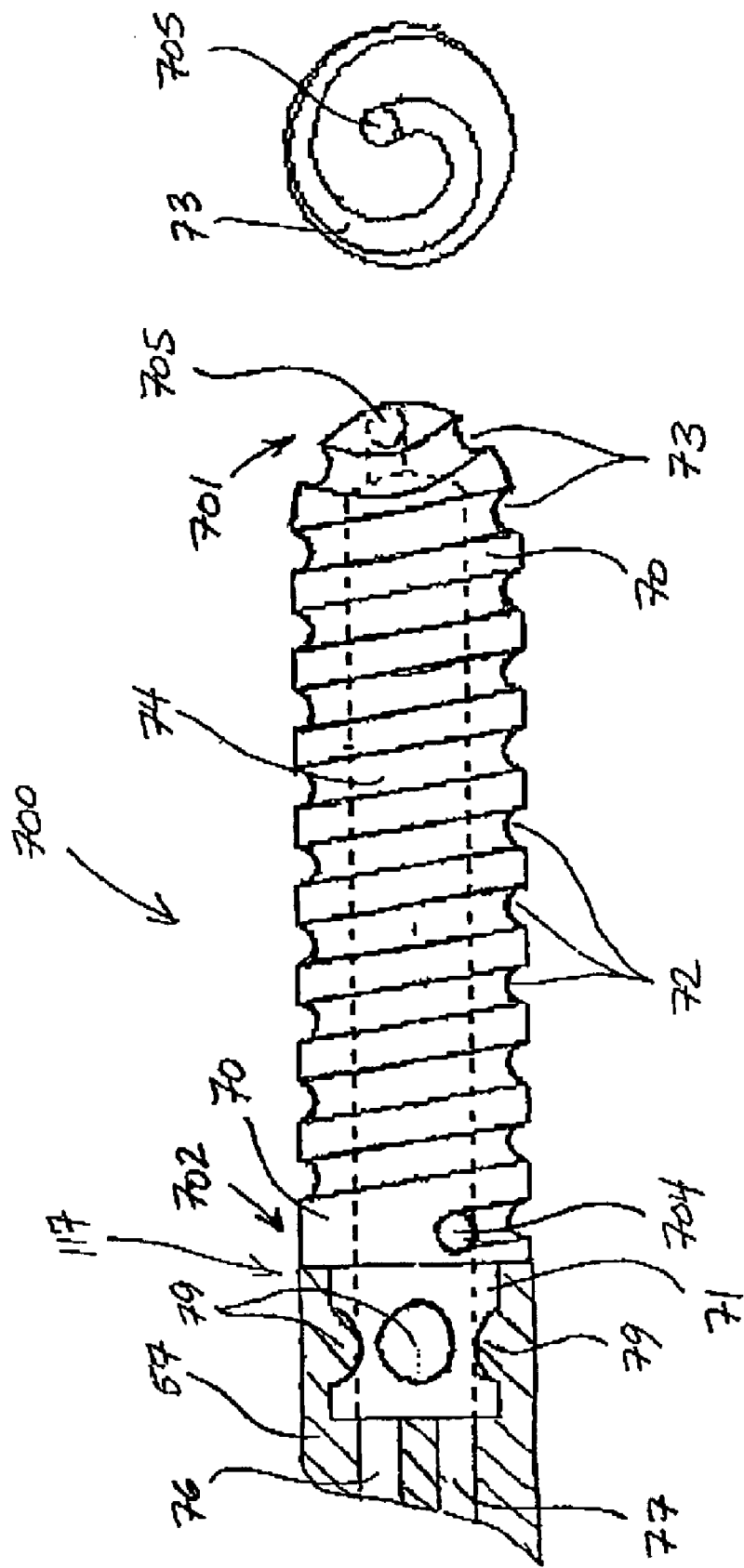
FIG. 7 is an end and plan view with partial section of an ablation catheter tip according to one embodiment of the present invention.

FIG. 7 is a plan view with partial section of an ablation catheter tip according to one embodiment of the present invention. Catheter tips 50, 500 illustrated in FIGS. 3B, 5B, and 6B–C are extensions of catheter shafts 5 (3B, 5B), 55 (6B), and 56 (6C) according to one group of embodiments and are components coupled to distal ends of the shafts according to another group of embodiments; one of the latter is illustrated in FIG. 7. FIG. 7 illustrates a tip 700 coupled to a distal end 117 of a catheter shaft 57 via interlocking features 79 formed in a proximal extension 71 of tip 700. Additional coupling means may be employed, for example a tubing band or adhesive bonding bridging a proximal end 702 of tip 700 and distal end 117 of shaft. According to one embodiment, tip 700 is formed of a flexible material, for example silicone, while, according to another embodiment, tip 700 is formed from a semi-rigid material, for example PEEK or Ultem; in either case, tip 700 is preferably formed from a biocompatible material resistant to high temperatures associated with RF ablation.

FIG. 7 further illustrates tip 700 including a side wall 70 in which a first helical groove 72 and a second helical groove 73 are formed to accommodate a first portion and a second portion, i.e. 162, 163, of a helical ablation electrode, i.e. 160; a first opening 704 in sidewall 70, located in proximity to proximal end 702 of tip 700, and a second opening 705 in sidewall 70, located in proximity to distal end 701 of tip 700, provide means for a first end and a second end, i.e. 161, 164, of the electrode to extend through sidewall 70 in order to provide fluid communication between one or more fluid delivery lumens of shaft 57 and a fluid lumen, i.e. 165, of the electrode. According to one embodiment, lumens 76 and 77 of shaft 57 are both fluid delivery lumens for delivering flow through and receiving flow from the electrode as previously described; according to an alternate embodiment just one of lumens 76, 77 is a fluid delivery lumen, delivering a fluid into the electrode, which fluid will exit the electrode exterior to shaft 57 and tip 700 as previously described. According to the latter embodiment, if opening 704 provides fluid communication, tip 700 may be solid rather than hollow as illustrated in FIG. 7. Although FIG. 7 illustrates tip 700 formed to accommodate positioning of an electrode thereover, additional embodiments of the present invention include a tip, such as tip 700, formed by injection molding material into a center of an electrode (any one of those described herein) to create an electrode assembly adapted to be joined to a distal end, i.e. distal end 117, of a catheter shaft, i.e. shaft 57.

Figure 8C:
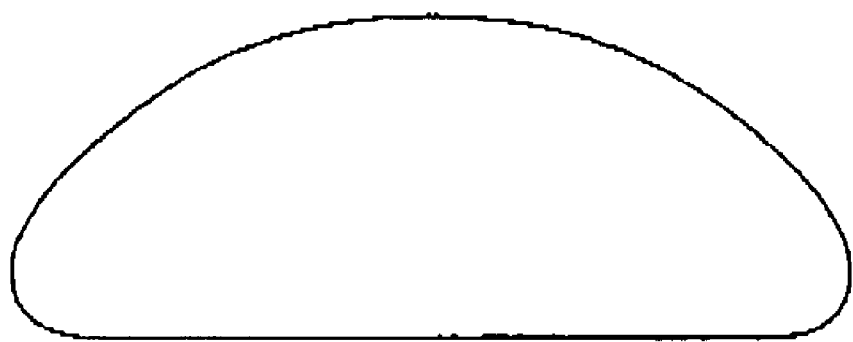
FIGS. 8A–C are schematics depicting alternate forms around which electrodes according to the present invention wind.
Figure 8B:
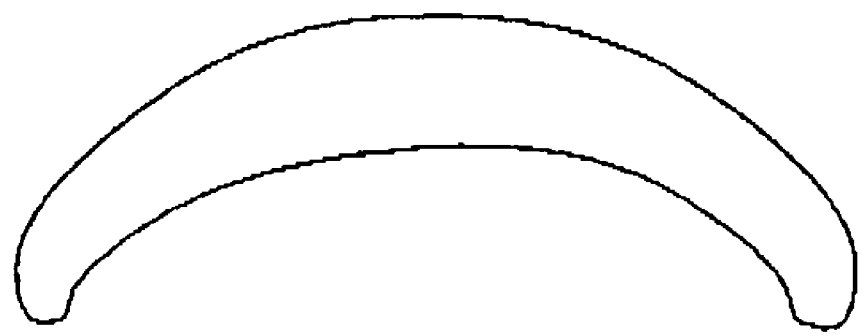
Figure 8A:
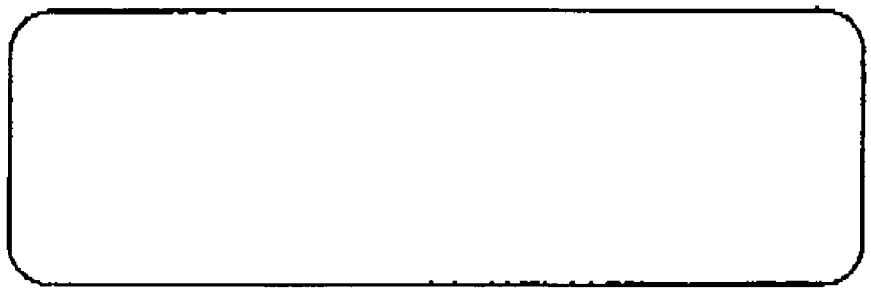

Although previous illustrations have depicted helical electrodes winding around a substantially cylindrical form, i.e. that with a circular cross-section (as illustrated in end views, i.e. FIG. 5A), alternate embodiments of the present invention include helical electrodes winding around alternate forms having various cross-sections, therefore it should be understood that the description 'helical' is not limited to circular cross-sections. FIG. 8A is a schematic depicting three exemplary cross-sections of alternate forms around which helical electrodes of the present invention may wind.

It should be appreciated that embodiments of the present invention, by incorporating an irrigated electrode terminating a distal end of an ablation catheter, facilitate both a formation of a discrete focal lesion and a formation of an elongated lesion by means of pushing or dragging the distal end of the ablation catheter over the tissue to be ablated.

In the foregoing detailed description, the invention has been described with reference to specific embodiments. However, it may be appreciated that various modifications and changes can be made without departing from the scope of the invention as set forth in the appended claims.

What is claimed is:

1. An irrigated ablation catheter assembly, comprising:
   a catheter shaft including a proximal end, a distal end, a fluid port in proximity to the proximal end, and a fluid delivery lumen extending from the port toward the distal end;
   a helical ablation electrode comprising a tube coupled to the catheter shaft and extending distally from the distal end of the catheter shaft, the electrode including a first end, a first portion extending from the first end and winding about a first diameter, a second portion extending from the first portion and winding about a second diameter smaller than the first diameter, a second end terminating the second portion, and a fluid lumen extending through the tube from a location in proximity to the first end to a location in proximity to the second end and in fluid communication with the fluid delivery lumen of the catheter shaft;
   wherein an irrigation fluid delivered through the fluid port of the catheter shaft passes through the fluid lumen of the ablation electrode to cool the electrode, and wherein the second end of the helical ablation electrode extends into the catheter shaft and provides the fluid communication between the fluid lumen of the electrode and the fluid delivery lumen of the catheter shaft.

2. The irrigated ablation catheter assembly of claim 1, wherein the tube includes an outer diameter and the electrode includes a pitch, the pitch approximately equal to the outer diameter of the tube.

3. The irrigated ablation catheter assembly of claim 1, wherein the tube includes an outer diameter and the electrode includes a pitch, the pitch greater than the outer diameter of the tube.

4. An irrigated ablation catheter assembly, comprising:
   a catheter shaft including a proximal end, a distal end, a fluid port in proximity to the proximal end, and a fluid delivery lumen extending from the port toward the distal end;
   a helical ablation electrode comprising a tube coupled to the catheter shaft and extending distally from the distal end of the catheter shaft; the electrode including a first end, a first portion extending from the first end and winding about a first diameter, a second portion extending from the first portion and winding about a second diameter smaller than the first diameter, a second end terminating the second portion, and a fluid lumen extending through the tube from a location in proximity to the first end to a location in proximity to the second end and in fluid communication with the fluid delivery lumen of the catheter shaft, wherein an irrigation fluid delivered through the fluid port of the catheter shaft passes through the fluid lumen of the ablation electrode to cool the electrode, wherein the first end of the helical ablation electrode extends into the catheter shaft and provides the fluid communication between the fluid lumen of the electrode and the fluid delivery lumen of the catheter shaft; and wherein the second end of the helical ablation electrode extends into the catheter shaft and provides the fluid communication between the fluid lumen of the electrode and the fluid lumen of the electrode and the fluid delivery lumen of the catheter shaft.

5. The catheter assembly of claim 4, wherein the fluid lumen of the helical ablation electrode opens exterior to the catheter shaft in proximity to the second end of the electrode.

6. The catheter assembly of claim 4, wherein the helical ablation electrode further includes a plurality of fluid exit ports positioned between the first end and the second end and the fluid lumen of the ablation electrode opens exterior to the catheter shaft at the plurality of fluid exit ports.

7. The catheter assembly of claim 6, wherein the second end of the helical ablation electrode extends into the catheter shaft and provides additional fluid communication between the fluid lumen of the electrode and the fluid delivery lumen of the catheter shaft.

8. The catheter assembly of claim 1, wherein the fluid lumen of the helical ablation electrode opens exterior to the catheter shaft in proximity to the first end of the ablation electrode.

9. The catheter assembly of claim 1, wherein the helical ablation electrode further includes a plurality of fluid exit ports positioned between the first end and the second end and the fluid lumen of the electrode opens exterior to the catheter shaft at the plurality of fluid exit ports.

10. An irrigated ablation catheter assembly, comprising:
    a catheter shaft including a proximal end, a distal end, a fluid port in proximity to the proximal end and a fluid delivery lumen extending from the port toward the distal end;
    a helical ablation electrode comprising a tube coupled to the catheter shaft and extending distally from the distal end of the catheter shaft; the electrode including a first end, a first portion extending from the first end and winding about a first diameter, a second portion extending from the first portion and winding about a second diameter smaller than the first diameter, a second end terminating the second portion, and a fluid lumen extending through the tube from a location in proximity to the first end to a location in proximity to the second end and in fluid communication with the fluid delivery lumen of the catheter shaft, wherein an irrigation fluid delivered through the fluid port of the catheter shaft passes through the fluid lumen of the ablation electrode to cool the electrode, wherein:
    the catheter shaft further includes a second fluid port in proximity to the proximal end and a second fluid delivery lumen extending from the second port toward the distal end of the shaft;
    the first end of the helical ablation electrode extends in the catheter shaft and provides the fluid communication between the fluid lumen of the electrode and the fluid delivery lumen of the catheter shaft; and
    the second end of the ablation electrode extends into the catheter shaft and provides additional fluid communication between the fluid lumen of the ablation electrode and the second fluid delivery lumen of the catheter shaft.

11. The catheter assembly of claim 10, wherein the fluid port is adapted to send fluid through the fluid delivery lumen of the catheter shaft to the fluid lumen of the ablation electrode and the second fluid pod is adapted to receive fluid through the second fluid delivery lumen of the catheter shaft from the fluid lumen of the ablation electrode.

12. The catheter assembly of claim 10, wherein the second fluid port is adapted to send fluid through the second fluid delivery lumen of the catheter shaft to the fluid lumen of the ablation electrode and the fluid port is adapted to receive fluid through the fluid delivery lumen of the catheter shaft from the fluid lumen of the ablation electrode.

13. An irrigated ablation catheter assembly, comprising:
a catheter shaft including a proximal end, a distal end, a fluid port in proximity to the proximal end, and a fluid delivery lumen extending from the port toward the distal end;
a helical ablation electrode comprising a tube coupled to the catheter shaft and extending distally from the distal end of the catheter shaft; the electrode including a first end, a first portion extending from the first end and winding about a first diameter, a second portion extending from the first portion and winding about a second diameter smaller than the first diameter, a second end terminating the second portion, and a fluid lumen extending through the tube from a location in proximity to the first end to a location in proximity to the second end and in fluid communication with the fluid delivery lumen of the catheter shaft, wherein an irrigation fluid delivered through the fluid port of the catheter shaft passes through the fluid lumen of the ablation electrode to cool the electrode; and
a tip, extending distally from the distal of the catheter shaft, which the helical ablation electrode winds about.

14. The catheter assembly of claim 13, wherein the tip further includes a sidewall and the first end of the ablation electrode extends through the sidewall to provide the fluid communication between the fluid lumen of the ablation electrode and the fluid delivery lumen of the catheter shaft.

15. The catheter assembly of claim 14, wherein the fluid lumen of the helical ablation electrode opens exterior to the tip in proximity to the second end of the electrode.

16. The catheter assembly of claim 14, wherein the helical ablation electrode further includes a plurality of fluid exit ports positioned between the first end and the second end and the fluid lumen of the ablation electrode opens exterior to the tip at the plurality of fluid exit ports.

17. The catheter assembly of claim 16, wherein the second end of the ablation electrode extends through the sidewall to provide additional fluid communication between the fluid lumen of the ablation electrode and the fluid delivery lumen of the catheter shaft.

18. The catheter assembly of claim 13, wherein the tip further includes a sidewall and the second end of the ablation electrode extends through the sidewall to provide the fluid communication between the fluid lumen of the ablation electrode and the fluid delivery lumen of the catheter shaft.

19. The catheter assembly of claim 18, wherein the fluid lumen of the helical ablation electrode opens exterior to the tip in proximity to the first end of the electrode.

20. The catheter assembly of claim 18, wherein the helical ablation electrode further includes a plurality of fluid exit ports positioned between the first end and the second end and the fluid lumen of the ablation electrode opens exterior to the tip at the plurality of fluid exit ports.

21. The catheter assembly of claim 13, wherein:
the catheter shaft further includes a second fluid port in proximity to the proximal end and a second fluid delivery lumen extending from the second port toward the distal end of the shaft;
the tip further includes a sidewall;
the first end of the ablation electrode extends through the sidewall of the tip to provide the fluid communication between the fluid lumen of the ablation electrode and the fluid delivery lumen of the catheter shaft; and
the second end of the ablation electrode extends through the sidewall of the tip to provide additional fluid communication between the fluid lumen of the ablation electrode and the second fluid delivery lumen of the catheter shaft.

22. The catheter assembly of claim 21, wherein the fluid port is adapted to send fluid through the fluid delivery lumen of the catheter shaft to the fluid lumen of the ablation electrode and the second fluid port is adapted to receive fluid through the second fluid delivery lumen of the catheter shaft from the fluid lumen of the ablation electrode.

23. The catheter assembly of claim 21, wherein the second fluid port is adapted to send fluid through the second fluid delivery lumen of the catheter shaft to the fluid lumen of the ablation electrode and the fluid port is adapted to receive fluid through the fluid delivery lumen of the catheter shaft from the fluid lumen of the ablation electrode.

24. The catheter assembly of claim 13, wherein the tip is an extension of the catheter shaft.

25. The catheter assembly of claim 13, wherein the tip is a component coupled to the distal end of the catheter shaft.

26. The catheter assembly of claim 13, wherein the tip comprises a flexible, temperature resistant and biocompatible polymer.

27. The catheter assembly of claim 13, wherein the tip comprises a solid core.

28. The catheter assembly of claim 13, wherein the tip comprises a hollow core.

29. The catheter assembly of claim 13, further comprising a filler material filling one or more gaps between windings of the helical ablation electrode.

30. The catheter assembly of claim 29, wherein the filler material comprises an electrically conductive material.

31. The catheter assembly of claim 29, wherein the filler material comprises an electrically insulative material.

32. A helical ablation electrode, comprising:
a first end;
a first portion extending from the first end and winding about a first diameter;
a second portion extending from the first portion and winding about a second diameter smaller than the first diameter;
a second end terminating the second portion;
a fluid lumen extending from a location in proximity to the first end to a location in proximity to the second end in fluid communication with an exterior surface of the electrode; and
a non-conductive tip around which the electrode winds, wherein an irrigation fluid passes through the fluid lumen of the ablation electrode to cool the electrode.

33. The helical ablation electrode of claim 32, further comprising a plurality of fluid exit ports positioned between the first end and the second end.

34. The catheter assembly of claim 32, wherein the tip comprises a flexible, temperature resistant and biocompatible polymer.

35. The catheter assembly of claim 32, wherein the tip comprises a solid core.

36. The catheter assembly of claim 32, wherein the tip comprises a hollow core.

37. The catheter assembly of claim 32, further comprising a filler material filling one or more gaps between windings of the helical ablation electrode.

38. The catheter assembly of claim 37, wherein the filler material comprises an electrically conductive material.

39. The catheter assembly of claim 37, wherein the filler material comprises an electrically insulative material.

* * * * *

UNITED STATES PATENT AND TRADEMARK OFFICE
CERTIFICATE OF CORRECTION

PATENT NO. : 7,156,843 B2
APPLICATION NO. : 10/657377
DATED : January 2, 2007
INVENTOR(S) : Skarda It is certified that error appears in the above-identified patent and that said Letters Patent is hereby corrected as shown below:

In column 8, line 34, please change "end and a" with --end, and a--.

In column 9, line 1, please change "fluid pod" with --fluid port--.

Signed and Sealed this

Ninth Day of October, 2007

JON W. DUDAS
*Director of the United States Patent and Trademark Office*